(12) United States Patent
Ueda et al.

(10) Patent No.: US 6,320,072 B1
(45) Date of Patent: Nov. 20, 2001

(54) METHOD FOR ISOLATION OF N-PROTECTED S-PHENYLCYSTEINE

(75) Inventors: Yasuyoshi Ueda, Himeji; Hiroshi Murao, Takasago; Koki Yamashita, Kobe; Koichi Kinoshita, Kakogawa, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/646,702

(22) PCT Filed: Jan. 21, 2000

(86) PCT No.: PCT/JP00/00274
§ 371 Date: Dec. 14, 2000
§ 102(e) Date: Dec. 14, 2000

(87) PCT Pub. No.: WO00/43360
PCT Pub. Date: Jul. 27, 2000

(30) Foreign Application Priority Data

Jan. 21, 1999 (JP) .................................................. 11-013388

(51) Int. Cl.[7] ...................... C07C 321/00; C07C 323/00; C07C 381/00
(52) U.S. Cl. ............................................. 562/431; 562/426
(58) Field of Search .................................................. 562/43

(56) References Cited

U.S. PATENT DOCUMENTS 5,543,564 * 8/1996 Kulpe et al. ........................ 562/467
6,011,170 * 1/2000 Kondo et al. ........................ 560/147

FOREIGN PATENT DOCUMENTS

11335351 * 12/1999 (JP) ........................................ 323/58
10029973 * 2/1998 (JP) ........................................ 323/59

* cited by examiner

*Primary Examiner*—Gary Geist
*Assistant Examiner*—Zachary Tucker
(74) *Attorney, Agent, or Firm*—Connolly Bove Lodge & Hutz (57) ABSTRACT

This invention provides a method of isolating N-protected-S-phenylcysteine (1) of high purity, expediently, efficiently and in good yield, which comprises causing said N-protected-S-phenylcysteine to be salted out in the form of a base salt in the presence of water.

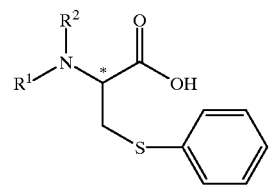

(1)

wherein $R^1$ represents an amino-protecting group; $R^2$ represents a hydrogen atom or, either independently of $R^1$ or taken together with $R^1$, represents an amino-protecting group.

21 Claims, 3 Drawing Sheets

METHOD FOR ISOLATION OF N-PROTECTED S-PHENYLCYSTEINE

CONTINUING DATA

This application is the national phase of PCT international application number PCT/JP00?00274, filed on Jan. 21, 2000.

TECHNICAL FIELD

The present invention relates to a method of isolating an N-protected-S-phenylcysteine of the following formula (1) [hereinafter referred to sometimes as N-protected-S-phenylcysteine (1)]. N-protected-S-phenylcysteines, such as N-benzyloxycarbonyl-S-phenyl-L-cysteine, are compounds of importance as synthetic intermediates of HIV-protease inhibitors as described in WO 96/23756 and EP 604185A1.

(1)

wherein $R^1$ represents an amino-protecting group; $R^2$ represents hydrogen or, either independently of $R^1$ or taken together with $R^1$, represents an amino-protecting group.

BACKGROUND ART

N-protected-S-phenylcysteine (1) can be synthesized by, for example, treating a compound of the formula (2):

(2)

(wherein $R^1$ and $R^2$ are as defined above; X represents a leaving group) with thiophenol under basic conditions as described in Japanese Application Hei-10-264397. By way of illustration, N-benzyloxycarbonyl-S-phenylcysteine can be synthesized by treating N-benzyloxycarbonyl-β-chloroalanine with thiophenol in an aqueous alkaline solution.

The N-protected-S-phenylcysteine (1) thus synthesized can be recovered typically by adding an acid to the basic aqueous solution thereof to precipitate the N-protected-S-phenylcysteine as a free acid. As a version of this technology, Japanese Kokai Publication Hei-10-29973 describes a process in which hydrochloric acid is added to an aqueous sodium hydroxide solution containing an N-benzyloxycarbonyl-S-phenylcysteine to cause the N-benzyloxycarbonyl-S-phenylcysteine to crystallize out as a free acid. In this process, the base salt of N-benzyloxycarbonyl-S-phenylcysteine (in this case, N-benzyloxycarbonyl-S-phenylcysteine sodium salt), which is readily soluble in water, is converted to the hardly-soluble free N-benzyloxycarbonyl-S-phenylcysteine by acidification. However, the process is not free from the disadvantage that, as pointed out in the same literature cited above, the free N-benzyloxycarbonyl-S-phenylcysteine tends to undergo gelation in the course of crystallization, and to fail in being crystallized in a good manner, in addition to the above problems, the process has also the problem that structurally related contaminant compounds cannot be easily removed. Thus, the methods heretofore known for crystallizing N-protected-S-phenylcysteine (1) as a free acid is not necessarily an effective isolation procedure.

SUMMARY OF THE INVENTION

Under the circumstances, the present invention has for its object to provide a method of isolating N-protected-S-phenylcysteine (1) of high purity, expediently, efficiently and in good yield.

The present invention, therefore, is directed to a method of isolating N-protected-S-phenylcysteine (1) which comprises causing said N-protected-S-phenylcysteine to be salted out in the form of a base salt in the presence of water.

The present inventors have discovered for the first time that a water-soluble base salt of N-protected-S-phenylcysteine (1) can be easily salted out in the presence of water with efficiency and in good yield and high purity.

The present invention is now described in detail.

DETAILED DESCRIPTION OF THE INVENTION

In the present specification, the term "base salt" as used with reference to N-protected-S-phenylcysteine means a compound such that a cation such as a metal ion and an ammonium ion has been substituted for the hydrogen ion of the carboxyl group of an N-protected-S-phenylcysteine. Moreover, the term "free" or "free acid" as used with reference to N-protected-S-phenylcysteine in this specification means that the N-protected-S-phenylcysteine has not formed a salt with any basic substance; stated differently that a hydrogen ion has been substituted for the cation, e.g. the metal ion or ammonium ion, of a base salt of N-protected-S-phenylcysteine or the compound in such condition.

The term "salting out" (and "salt out") as used with reference to a base salt of N-protected-S-phenylcysteine in this specification means that the base salt of N-protected-S-phenylcysteine is caused to separate out from an aqueous solution containing the salt by causing another substance (chiefly an inorganic salt) to be present in said aqueous solution.

In the above formula (1), $R^1$ represents an amino-protecting group. $R^2$ represents a hydrogen atom or, either independently of $R^1$ or taken together with $R^1$, an amino-protecting group.

In the method of the present invention, it is essential that an amino-protecting group be present on S-phenylcysteine.

The above-mentioned amino-protecting group is not particularly restricted but may, for instance, be a group selected from among the protective groups mentioned in Protective Groups in Organic Synthesis, 2nd Ed., John Wiley & Sons (1991) as well as an alkyl, aralkyl or aryl group.

When a further derivatization of N-protected-S-phenylcysteine (1) is contemplated, an urethane-type or acyl-type protective group capable of masking the basicity of the amino group is preferably used. Among specific examples of such protective groups, there can be mentioned benzyloxycarbonyl, ethoxycarbonyl, methoxycarbonyl, tert-butoxycarbonyl, acetyl, tosyl, benzoyl and phthaloyl, among others. Moreover, (3S)-tetrahydrofuranyloxycarbonyl and 3-hydroxy-2-methylbenzoyl whose hydroxyl group may optionally be protected can also be selectively employed. Particularly, urethane-type protective groups are preferred and aralkyloxycarbonyl and lower alkoxycarbonyl groups are still more preferred. More particularly, benzyloxycarbonyl, tert-butoxycarbonyl, methoxycarbonyl and ethoxycarbonyl are preferred and, among them, benzyloxycarbonyl is still more preferred. When the amino-protecting group is a benzyloxycarbonyl group, N-protected-S-phenylcysteine (1) is a compound of great importance as a synthetic intermediate of HIV-protease inhibitors as described in WO 96/23756 and EP 604185A1, for instance.

N-protected-S-phenylcysteine (1) may be an optically active compound. Even when such an optically active compound is used in the present invention, the salting out can be achieved without detracting from optical purity.

The base salt of N-protected-S-phenylcysteine (1) is not particularly restricted but includes, among others, the metal salts, such as alkali metal salts, e.g. lithium salt, sodium salt, potassium salt, etc., alkaline earth metal salts, and ammonium salts of N-protected-S-phenylcysteine (1). Among them, the metal salts are preferred, the alkali metal salts are particularly preferred, and the sodium salt is most preferred.

The base for use in converting N-protected-S-phenylcysteine (1) to its base salt is not particularly restricted but includes alkali metal hydroxides, alkali metal carbonates, alkali metal hydrogencarbonates, alkaline earth metal hydroxides, alkaline earth metal carbonates, and ammonia, among others. Preferred are alkali metal hydroxides, alkali metal carbonates and alkali metal hydrogencarbonates. More particularly, sodium hydroxide, potassium hydroxide, lithium hydroxide, sodium carbonate, potassium carbonate, lithium carbonate, sodium hydrogencarbonate and potassium hydrogencarbonate can be mentioned. The most preferred is sodium hydroxide.

The preferred method for converting N-protected-S-phenylcysteine (1) to a base salt comprises reacting the N-protected-S-phenylcysteine (1) with said base under neutral to basic conditions. In terms of pH, the system should be maintained at not less than pH 7, preferably not less than pH 8, more preferably not less than pH 9, in order to retain the stability of the amino-protecting group. Generally speaking, the reaction can be conducted with advantage in the neighborhood of pH 9 to 11. The use of a pH less than 7 is objectionable because such a pH level induces conversion of the base salt of N-protected-S-phenylcysteine to free N-protected-S-phenylcysteine. Moreover, when the amino-protecting group is a protective group which is not so stable under basic conditions, such as trifluoroacetyl, it is advisable to avoid strongly basic conditions, for example pH 12 or higher.

In the present invention, said salting out is carried out in the presence of water. Generally, it is carried out in an aqueous solution of N-protected-S-phenylcysteine (1). Because N-protected-S-phenylcysteine (1) is caused to be present in the form of its salt with a base, this procedure is preferably carried out under basic conditions.

Within the range not interfering with the procedure, said aqueous solution may contain an organic solvent or the like. The organic solvent mentioned just above is not particularly restricted but includes, among others, esters of acetic acid, such as ethyl acetate, isopropyl acetate, etc.; aromatic hydrocarbons represented by toluene; aliphatic hydrocarbons such as hexane, heptane, etc.; ethers such as methyl tert-butyl ether, di-n-butyl ether, tetrahydrofuran, etc.; alcohols such as methanol; and ketones such as acetone, 2-butanone and so on. By causing such an organic solvent to be present in the system, the dissolution and removal of fat-soluble (lipophilic) impurity coexistent with said salt can be facilitated. The organic solvent may be caused to be present from the beginning of salting out or added when the salting out has progressed to a sufficient extent.

In order that the base salt of N-protected-S-phenylcysteine may be salted out, another salt must be caused to be present in the system. This salt is preferably an inorganic salt. The inorganic salt is not particularly restricted but includes alkali metal salts such as sodium chloride, potassium chloride, sodium sulfate, potassium sulfate, etc.; ammonium sulfate, ammonium chloride and calcium chloride, among others. From the standpoint of ease of use, alkali metal salts are preferred and sodium chloride and sodium sulfate are still more preferred. Of all of them, sodium chloride is most preferred in consideration of its low cost, the ease of handling, ease of waste water disposal, the efficiency of salting out the base salt of N-protected-S-phenylcysteine, and the properties of the salt obtained, among other factors. The salt mentioned above may be added to the system or, taking advantage of the neutralization reaction between an acid and a base, may be caused to form in the system.

The cation of the salt to be used for salting out is preferably of the same species as the cation of the base salt of N-protected-S-phenylcysteine. N-benzyloxycarbonyl-S-phenylcysteine, for instance, is preferably salted out as the sodium salt. In this case, the salt to be used for salting out is preferably a sodium salt such as sodium chloride, sodium sulfate and the like, and most preferred is sodium chloride.

The amount of the salt to be used for this salting out procedure depends on species of the salt and species and amount of said base salt of N-protected-S-phenylcysteine, among other variables, and cannot be defined in general terms. However, it is preferred to use a sufficient amount of a salt to attain the objective salting out in good yield. More particularly, the inorganic salt is preferably caused to be present at the amount of about 5 weight % or more in terms of the concentration in water. The upper limit is generally the saturation point. Taking sodium chloride as an example, the salting out can be carried out with advantage at a concentration somewhere between about 5 weight % and the point of saturation.

The concentration of the base salt of N-protected-S-phenylcysteine (1) for salting out is not particularly restricted but is generally not more than about 30 weight %, preferably within the range of 5 to 20 weight %, based on the water in the system.

In order that the base salt of N-protected-S-phenylcysteine may be salted out easily and efficiently, it is preferred to insure that the system contains both the base salt of N-protected-S-phenylcysteine and a salt used for salting out in effective amounts (sufficient amounts necessary for salting out). Thus, it is preferred that the salting out is effected by;

i) increasing the amount of presence of said base salt of N-protected-S-phenylcysteine with the amount of presence of said inorganic salt being kept constant,
ii) increasing the amount of presence of said inorganic salt, with the amount of presence of said base salt of N-protected-S-phenylcysteine being kept constant, or
iii) increasing the amount of said base salt of N-protected-S-phenylcysteine, with the amount of presence of said inorganic salt being simultaneously increased.

The temperature of the salting out is not particularly restricted but may for example be somewhere between the solidification temperature of the system to about 100° C., preferably about 0° C. to 60° C. Particularly, the procedure can be followed with advantage within the range of about 10° C. to about 50° C.

If the base salt of N-protected-S-phenylcysteine (1) is not smoothly salted out, seed crystals may be added to the system.

As mentioned above, Japanese Kokai Publication Hei-10-29973 discloses a technology wherein a basic (pH 10 to 11) aqueous solution containing a base salt (sodium salt) of N-benzyloxycarbonyl-S-phenylcysteine is acidified with hydrochloric acid to crystallize N-benzyloxycarbonyl-S-phenylcysteine as the free acid. However, the concentration of sodium chloride in said basic aqueous solution is as low as less than 3 weight % which is not sufficient to effect salting out. Moreover, in acidification, the base salt (sodium salt) of N-benzyloxycarbonyl-S-phenylcysteine is converted to the free acid before the amount of presence of the inorganic salt (sodium chloride) is increased by neutralization reaction so that the base salt of N-benzyloxycarbonyl-S-phenylcysteine is not salted out.

The method of the present invention can be used for the purpose of purifying a free N-protected-S-phenylcysteine or a base salt of N-protected-S-phenylcysteine or for the purpose of separating an N-protected-S-phenylcysteine in the form of a base salt from the reaction mixture.

When, for such purposes, an aqueous medium containing a sufficient amount of an inorganic salt for effecting salting out under basic conditions, for instance, is used, the formation of the base salt of N-protected-S-phenylcysteine and the salting out of the thus-formed base salt of N-protected-S-phenylcysteine can be concurrently accomplished. In this case, too, the formation of the base salt of N-protected-S-phenylcysteine and, at the same time, the salting out thereof can be expedited by causing seed crystals to be present in the system.

Furthermore, it is possible to synthesize an N-protected-S-phenylcysteine by carrying out the synthetic reaction under basic conditions and, at the same time, causing the resulting N-protected-S-phenylcysteine to be salted out from the reaction mixture in the form of a base salt. This procedure contributes to improvements in the yield and/or quality of N-protected-S-phenylcysteine because the decomposition and racemization of the N-protected-S-phenylcysteine which is not necessarily stable under basic conditions can be prevented. Furthermore, the base salt of N-protected-S-phenylcysteine can be selectively salted out from a reaction mixture containing structural analogs and other impurities capable of forming salts with the base used, with the result that the product can be purified by removing said impurities into an aqueous phase with high efficiency.

More particularly, in an aqueous medium in which an inorganic salt is present in a sufficient amount for effecting salting out under basic conditions, a compound of the formula (2):

(2)

(wherein $R^1$ and $R^2$ are as defined above; X represents a leaving group) is treated with thiophenol to give an N-protected-S-phenylcysteine and, at the same time, the N-protected-S-phenylcysteine is salted out in the form of a base salt from the reaction mixtures (that is to say the N-protected-S-phenylcysteine is removed from the reaction system as the base salt). In this manner, the N-protected-S-phenylcysteine which is not necessarily stable enough under basic conditions is protected against decomposition and racemization, with the result that the N-protected-S-phenylcysteine of high purity can be obtained in high yield. Of course, the base, basic conditions, inorganic salt, etc. to be used in this process are the same as those mentioned hereinbefore.

The leaving group represented by X is not particularly restricted but includes halogen, e.g. chloro; alkylsulfonyloxy groups containing 1 to 10 carbon atoms, e.g. mesyloxy; arylsulfonyloxy groups containing 6 to 10 carbon atoms, e.g. tosyloxy; aralkylsulfonyloxy groups containing 7 to 10 carbon atoms; acetyloxy, trihaloacetyloxy and phosphoryl, among others.

In carrying out the salting out for the purpose of improving the quality of the product, the fat-soluble (lipophilic) contaminants can be dissolved and removed by supplementing the system with an organic solvent (an acetic acid ester, e.g. ethyl acetate, isopropyl acetate, etc.; anomatic hydrocarbon, e.g. toluene; an aliphatic hydrocarbon, e.g. hexane, heptane, etc.; an ether, e.g. methyl tert-butyl ether, di-n-butyl ether, tetrahydrofuran, etc.; an alcohol, e.g. methanol; or a ketone, e.g. acetone, 2-butanone, etc., among others). This practice is particularly effective for salting out from a reaction mixture such as a reactive crystallization, for instance. The organic solvent may be caused to be present from the beginning of salting out or added after the salting out has progressed fairly far enough.

The base salt of N-protected-S-phenylcysteine as salted out by the method of the present invention can be recovered by a separatory procedure such as filtration. The recovered base salt of N-protected-S-phenylcysteine can be washed with water [e.g. cold water or water containing the salt used for salting out (e.g. an aqueous solution of sodium chloride) is preferred] or said organic solvent and, where necessary, the solvent such as water may be removed at atmospheric pressure or under reduced pressure. The salting out yield is usually not less than 80%, preferably not less than 90%, and more preferably approximately 100%.

The resulting base salt of N-protected-S-phenylcysteine can be neutralized with an acid such as hydrochloric acid and sulfuric acid to provide the N-protected-S-phenylcysteine in the free form. By mixing this free N-protected-S-phenylcysteine with an organic solvent, said mixture of an organic solvent and free-N-protected-S-phenylcysteine can be obtained. The organic solvent mentioned just above is not particularly restricted but includes esters of acetic acid, such as ethyl acetate, isopropyl acetate, etc.; aromatic hydrocarbons such as toluene etc.; and ethers such as methyl tert-butyl ether, di-n-butyl ether, tetrahydrofuran, etc., among other solvents. Needless to say, the neutralization with said acid can be carried out in the presence of said organic solvent. The thus-prepared mixture of an organic solvent with a free N-protected-S-phenylcysteine (e.g. a mixture of toluene and free-N-protected-S-phenylcysteine) can be used for further derivatization (e.g. esterification with an alcohol).

BEST MODE FOR CARRYING OUT THE INVENTION

The following examples, comparative and reference examples are intended to illustrate the present invention in further detail and should by no means be construed as defining the scope of the invention. The quantitative analyses performed for S-phenylcysteine derivatives in the following examples were invariably carried out using an HPLC equipped with a UV detector.

EXAMPLE 1

To 137.8 g of N-benzyloxycarbonyl-S-phenyl-L-cysteine was added 56.4 g of a 30 wt. % solution of sodium hydroxide (1.0 mole per mole of N-benzyloxycarbonyl-S-phenyl-L-cysteine) in 300 ml of water, and the mixture was adjusted to pH 10.2 and stirred under warming at about 40° C. for 1 hour to prepare a clear solution. Then, 73.5 g of sodium chloride (22 wt. % based on water) was added and the stirring was continued for 1 hour, whereupon crystals separated out. The crystal crop was harvested by suction filtration to give 312.2 g of wet crystals of N-benzyloxycarbonyl-S-phenyl-L-cysteine. HPLC analysis showed that the crystallization yield was 100%.

Reference Example 1

The wet crystals of N-benzyloxycarbonyl-S-phenyl-L-cysteine sodium salt obtained in Example 1 (310.0 g) were dissolved in 700 ml of water and the water was then evaporated under reduced pressure at about 50° C. for concentration to 619.5 g to thereby cause crystals to separate out. The crystal crop was recovered by suction filtration and rinsed with 100 ml of water to give 208 g of wet crystals.

The whole amount of the wet crystals thus obtained was dissolved in 600 ml of water and the water was then evaporated under reduced pressure at about 50° C. to give 209.5 g of concentrate. This oily concentrate was crystallized by adding 1000 ml of acetone. The crystal crop was recovered by suction filtration and washed with 200 ml of acetone to give 88.8 g of wet crystals.

These crystals were further dissolved in 400 ml of water and, then, recrystallized by adding 2800 ml of acetone. The resulting crystals were recovered by suction filtration, washed with 1300 ml of acetone, and finally dried in vacuo (1 to 30 mm Hg, 20 to 40° C., 20 hr.) to give 44.5 g of crystals. This crystalline product contained 43.8 g of N-benzyloxycarbonyl-S-phenyl-L-cysteine sodium salt and its purity was 98.4 wt. % (as assayed by HPLC for free N-benzyloxycarbonyl-S-phenyl-L-cysteine and calculated as sodium salt).

The 400 MHz nuclear magnetic resonance spectrum of this N-benzyloxycarbonyl-S-phenyl-L-cysteine sodium salt [$D_2O$, sodium 3-(trimethylsilyl)-propanesulfonate as internal standard] was:

δ (ppm): 3.19 (1H, dd, J=8.1, 13.9 Hz), 3.51 (1H, dd, J=3.4, 13.9 Hz), 4.15 (1H, dd, J=3.4, 8.1 Hz), 4.89–5.01 (2H, ABq, J=12.4 Hz), 7.2–7.4 (10H, m).

Figure 1:
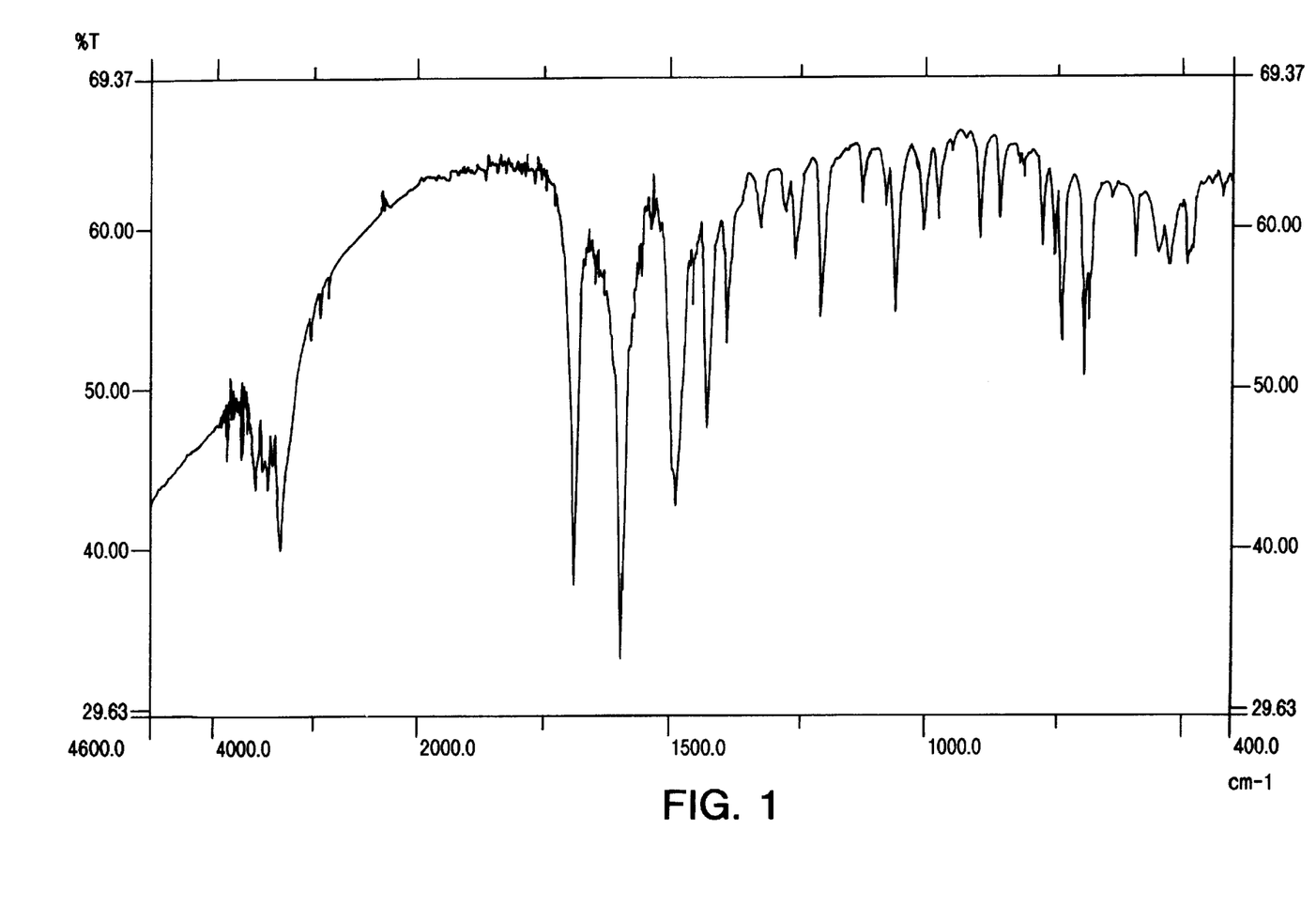
FIG. 1 is an infrared absorption spectrum (KBr disk) of the N-benzyloxycarbonyl-S-phenyl-L-cysteine sodium salt obtained.
Figure 2:
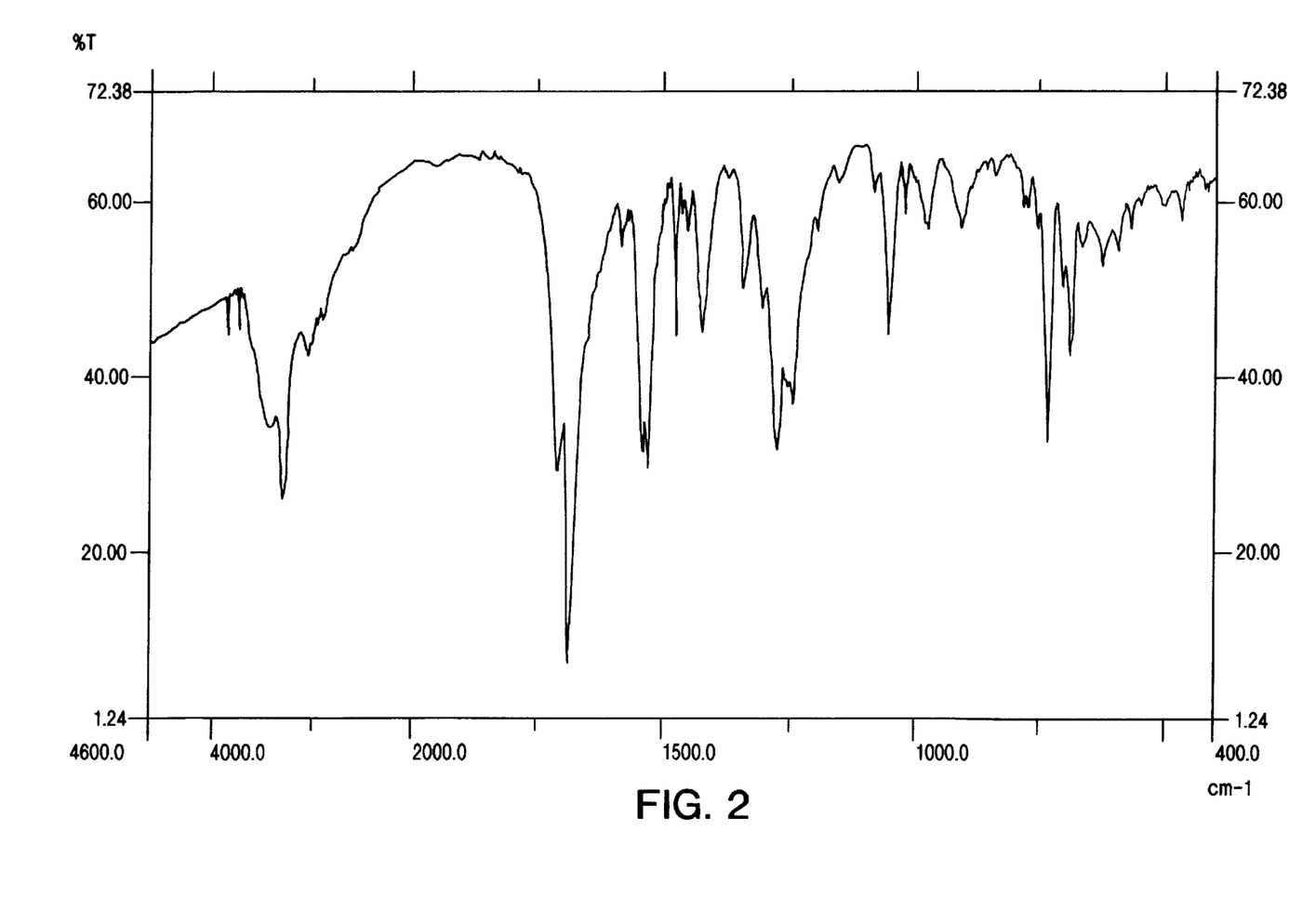
FIG. 2 is an infrared absorption spectrum (KBr disk) of free N-benzyloxycarbonyl-S-phenyl-L-cysteine.

The infrared absorption spectrum (KBr disk) of the above N-benzyloxycarbonyl-S-phenyl-L-cysteine sodium salt is presented in FIG. 1. As a reference, an infrared absorption spectrum (KBr disk) of free N-benzyloxycarbonyl-S-phenyl-L-cysteine is presented in FIG. 2.

EXAMPLE 2

Using 3 g of the crystals of N-benzyloxycarbonyl-S-phenyl-L-cysteine sodium salt prepared in Reference Example 1, (A) a solution thereof in 30 ml of water and (B) a suspension thereof in 30 ml of a 20 wt. % aqueous solution of sodium chloride were prepared. The solution and suspension were respectively adjusted to pH 9.7 with a 3 wt. % aqueous solution of sodium hydroxide and stirred at 40° C. Each solution was serially sampled and analyzed by HPLC for the concentration of N-benzyloxycarbonyl-S-phenyl-L-cysteine sodium salt in the sample to monitor the percentage of remaining N-benzyloxycarbonyl-S-phenyl-L-cysteine sodium salt.

Figure 3:
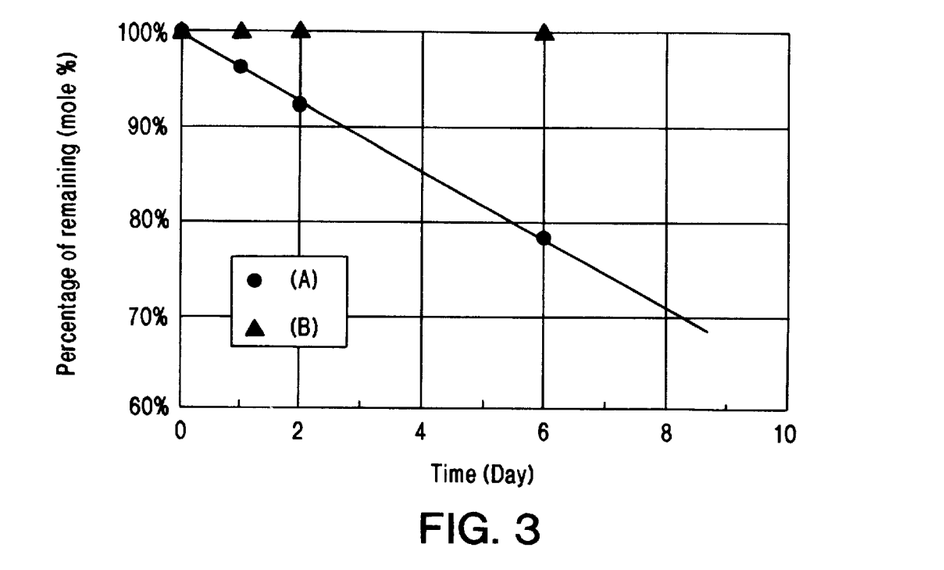
FIG. 3 is a graph showing the time course of the percentage of remaining N-benzyloxycarbonyl-S-phenyl-L-cysteine sodium salt at 40° C.

FIG. 3 shows the time course of the percentage of remaining N-benzyloxycarbonyl-S-phenyl-L-cysteine sodium salt at 40° C.

The above result indicates that the sodium salt of N-benzyloxycarbonyl-S-phenyl-L-cysteine which is unstable under basic conditions can be stabilized by the above salting out procedure.

EXAMPLE 3

To 86.19 g of an aqueous solution containing 7.47 g of β-chloroalanine was added 11.35 g of benzyloxycarbonyl chloride (1.1 moles per mole of β-chloroalanine) dropwise over 1 hour under constant stirring at about 5° C., with the reaction system being maintained at pH 9.7 with a 30% aqueous solution of sodium hydroxide. The reaction was further continued for 3 hours, at the end of which time the reaction mixture was washed with 50 ml of toluene. This washed reaction mixture, 89.53 g, contained 15.52 g (yield 100%) of N-benzyloxycarbonyl-β-chloroalanine.

To 88.27 g of the above reaction mixture (which contained 15.30 g of N-benzyloxycarbonyl-β-chloroalanine) was added 13.95 g of sodium chloride (25 wt. % based on water), and, thereafter, 9.82 g of thiophenol (1.5 moles per mole of N-benzyloxycarbonyl-β-chloroalanine) was added dropwise over 1 hour with constant stirring under nitrogen atmosphere at about 40° C., with the reaction system being maintained at pH about 10 with a 30% aqueous solution of sodium hydroxide. With progress of the reaction, the reaction product N-benzyloxycarbonyl-S-phenyl-L-cysteine was crystallized as the sodium salt and the reaction mixture became slurry-like. The slurry obtained after 20 hours of reaction, 148.97 g, contained 19.21 g (reaction yield 98%) of N-benzyloxycarbonyl-S-phenyl-L-cysteine.

EXAMPLE 4

To 5.0 g of purified N-benzyloxycarbonyl-β-chloroalanine was added 32 g of water, followed by addition of sodium chloride [A: 0.0 g (no addition) or B: 8.0 g (25 wt. % concentration based on water)]. To this solution, 3.2 g of thiophenol (1.5 moles per mole of N-benzyloxycarbonyl-β-chloroalanine) was added dropwise over 1 hour with constant stirring under nitrogen atmosphere at about 40° C., with the reaction system being maintained at pH about 10 with a 30% aqueous solution of sodium hydroxide. The reaction was further continued for 20 hours and the N-benzyloxycarbonyl-S-phenyl-L-cysteine content of the reaction mixture was determined. The yield was then calculated.

The concentrations of sodium chloride in water and the corresponding yields of N-benzyloxycarbonyl-S-phenyl-L-cysteine are summarized in Table 1.

TABLE 1

|  | A | B |
|---|---|---|
| Concentration of sodium chloride (before reaction) | 0 wt. % | 25 wt. % |
| Concentration of sodium chloride (after reaction) | 3 wt. % | 28 wt. % |
| Yield of N-carbobenzoxy-S-phenyl-L-cysteine | 89 mol % | 97 mol % |

In the absence of sodium chloride (A), the reaction system did not form a slurry. In contrast, a slurry was formed in the presence of sodium chloride (B).

It can be seen from the above result that addition of sodium chloride promotes salting out of the N-benzyloxycarbonyl-S-phenyl-L-cysteine sodium salt formed to thereby purge it out from the reaction field and protect the product effectively against decomposition.

Comparative Example 1

To 141.22 g of a reaction product slurry obtained in the same manner as in Example 3 (which contained 18.41 g of N-benzyloxycarbonyl-S-phenyl-L-cysteine), 17.44 g (3.0 moles per mole of N-benzyloxycarbonyl-S-phenyl-L-cysteine) of concentrated hydrochloric acid was added dropwise over 5 hours under nitrogen atmosphere at about 25° C. with constant stirring so as to adjust the slurry to pH 3. The mixture was further stirred at the same temperature for 3 hours to effect a thorough crystallization. The crystals were harvested by suction filtration and rinsed with water to give 26.11 g of wet crystals. This crystal crop contained 18.19 g of N-benzyloxycarbonyl-S-phenyl-L-cysteine (crystallization yield 99%) and its apparent purity on HPLC was 74.8 area %.

EXAMPLE 5

To 145.34 g of the reaction slurry obtained in Example 3 (which contained 18.73 g of N-benzyloxycarbonyl-S-phenyl-L-cysteine) was added 65 ml of toluene, and the mixture was stirred at about 40° C. under nitrogen atmosphere for 1 hour. The resulting crystals were harvested by suction filtration and the wet crystals thus obtained were washed serially with toluene and saturated aqueous sodium chloride solution and dried in vacuo (1 to 30 mmHg, 20 to 40° C., for 20 hours) to give 21.96 g of crystals. This crystal crop contained 19.67 g of N-benzyloxycarbonyl-S-phenyl-L-cysteine sodium salt (crystallization yield 99%) and its apparent purity on HPLC was 99.0 area %. Compared with the case in which N-benzyloxycarbonyl-S-phenyl-L-cysteine was crystallized in the form of free acid (Comparative Example 1), the amount of impurity detected by HPLC was extremely small, indicating that N-benzyloxycarbonyl-S-phenyl-L-cysteine of high quality could be obtained in the form of a base salt.

EXAMPLE 6

Figure 4:
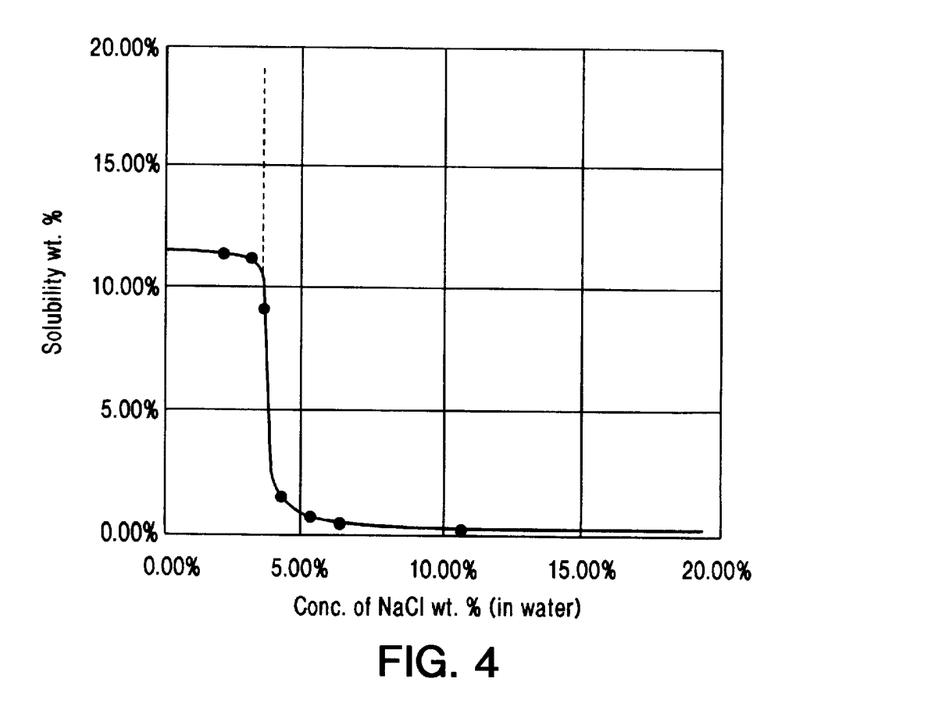
FIG. 4 is a graph showing the solubility of N-benzyloxycarbonyl-S-phenyl-L-cysteine sodium salt as plotted against sodium chloride concentration.

Under constant addition of sodium chloride to 190.89 g of an aqueous solution (pH 10.8) prepared from 20.04 g of N-benzyloxycarbonyl-S-phenyl-L-cysteine and 8.04 g (1.0 mole per mole of N-benzyloxycarbonyl-S-phenyl-L-cysteine) of sodium hydroxide, the solution was serially sampled and the weight % concentration (solubility) of N-benzyloxycarbonyl-S-phenyl-L-cysteine sodium salt in the filtrate remaining after removal of crystals was determined. The solubility of N-benzyloxycarbonyl-S-phenyl-L-cysteine sodium salt as plotted against the concentration of sodium chloride is shown in FIG. 4.

EXAMPLE 7

In 20 ml of water were dissolved 2.05 g of N-benzyloxycarbonyl-S-phenyl-L-cysteine and 0.26 g (1.0 mole per mole of N-benzyloxycarbonyl-S-phenyl-L-cysteine) of lithium hydroxide monohydrate. To this solution was added 7.08 g (35 weight % based on water) of lithium chloride, and the mixture was shaken for 10 minutes. As a result, crystals separated out.

EXAMPLE 8

In 20 ml of water was suspended 2.02 g of N-benzyloxycarbonyl-S-phenyl-L-cysteine, and 28 wt. % aqueous ammonia was added until complete dissolution occurred to give 21.93 g of an aqueous solution at pH 9.2. To this solution was added 1.01 g (5 wt. % based on water) of ammonium chloride, and the mixture was shaken for 10 minutes. As a result, crystals separated out.

EXAMPLE 9

To 45.52 g of an aqueous solution (pH 10.8) containing 5.04 g of N-benzyl-S-phenylcysteine and 2.38 g of sodium hydroxide (1.0 mole per mole of N-benzyl-S-phenylcysteine) was added 9.71 g (24 wt. %/$H_2O$) of sodium chloride, and the mixture was stirred for 1 hour. As a result, crystals separated out.

Comparative Example 2

To 46.85 g of an aqueous solution (pH 10.8) containing 5.12 g of S-phenyl-L-cysteine and 3.55 g of sodium hydroxide (1.0 mole per mole of S-phenyl-L-cysteine) was added 12.29 g (30 wt. %/$H_2O$) of sodium chloride. As a result, there occurred no salting out of S-phenyl-L-cysteine sodium salt, nor any change induced in the state of the solution.

The above result indicates that, in the present invention, the presence of a protective group on the amino group is indispensable.

Comparative Example 3

To 62.31 g of an aqueous solution containing 4.55 g of S-phenyl-L-cysteine and maintained at pH 11 with a 30% aqueous solution of sodium hydroxide under constant stirring at about 25° C., 3.94 g of benzyloxycarbonyl chloride (1.0 mole per mole of S-phenyl-L-cysteine) was added dropwise over 1 hour. The mixture was allowed to react for a further 12 hours. The resulting reaction mixture weighed 67.19 g, had a pH value of 10.9, and contained 7.12 g of N-benzyloxycarbonyl-S-phenyl-L-cysteine (concentration 10.6 wt. %; yield 93%). The concentration of sodium chloride in the reaction mixture was 2.7 weight % (based on water). This reaction mixture showed no salting out of N-benzyloxycarbonyl-S-phenyl-L-cysteine sodium salt.

EXAMPLE 10

To 14.98 g of the crystals of N-benzyloxycarbonyl-S-phenyl-L-cysteine sodium salt obtained in Example 5 (purity 13.42 g) were added 50 ml of water and 260 ml of toluene, and the mixture was adjusted to pH 1.8 with concentrated hydrochloric acid at about 40° C. with stirring. The aqueous layer was discarded after phase separation and the toluene layer weighing 236.65 g was recovered. This toluene solution contained 2.54 g (recovery rate 100%) of N-benzyloxycarbonyl-S-phenyl-L-cysteine.

To 235.14 g of this toluene solution (which contained 12.46 g of N-benzyloxycarbonyl-S-phenyl-L-cysteine) was added 0.66 g of p-toluenesulfonic acid monohydrate, and using a total of 25.99 g of methanol, the reaction was carried out under reflux for 20 hours, with the byproduct water being azeotropically distilled off. This reaction mixture was cooled to about 30° C. to give 91.99 g of a reaction mixture. This reaction mixture contained 12.50 g of N-benzyloxycarbonyl-S-phenyl-L-cysteine methyl ester. The yield was 96%.

EXAMPLE 11

In 160 ml of water was dissolved 15.7 g (98.1 mmol) of β-chloro-L-alanine hydrochloride. After cooling to an internal temperature of 0 to 5° C., the solution was adjusted to pH 10 by adding about 36 g of a 30 wt. % aqueous solution of sodium hydroxide dropwise with vigorous stirring. Then, with the internal temperature being maintained at 0 to 5° C. under vigorous stirring, 20.5 g (120.0 mmol) of benzyl chloroformate was added dropwise over 1 hour and the mixture was further stirred for 4 hours. During the reaction, the reaction mixture was maintained at pH 9.5 to 10.5 by adding about 16 g of a 30 wt. % aqueous solution of sodium hydroxide dropwise. HPLC assay showed that this reaction mixture contained 25.1 g (97.5 mmol) of N-carbobenzyloxy-β-chloro-L-alanine.

To the above reaction mixture was added 22.0 g (200.0 mmol) of thiophenol dropwise under nitrogen atmosphere with intense stirring. During this procedure, the reaction mixture was maintained at pH 9.7 to 10.3 by adding about 26 g of a 30 wt. % aqueous solution of sodium hydroxide dropwise. The internal temperature was then increased to 50° C. and the reaction was conducted under nitrogen atmosphere for 3.5 hours. During the reaction, the reaction mixture was maintained at pH 9.7 to 10.3 by adding about 1 g of a 30 wt. % aqueous solution of sodium hydroxide dropwise. During this reaction, the product N-carbobenzyloxy-S-phenyl-L-cysteine (N-benzyloxycarbonyl-S-phenyl-L-cysteine) was salted out in the form of sodium salt so that the reaction system became slurry-like. To this slurry was added about 20 g of concentrated hydrochloric acid gradually over 3 hours with vigorous stirring under nitrogen atmosphere until the system became pH 3. The crystals of N-carbobenzyloxy-S-phenyl-L-cysteine were recovered by suction filtration, rinsed with 100 ml of water twice and drained thoroughly to give wet crystals of N-carbobenzyloxy-S-phenyl-L-cysteine [29.8 g (89.9 mmol) of pure N-carbobenzyloxy-S-phenyl-L-cysteine]. The optical purity of the N-carbobenzyloxy-S-phenyl-L-cysteine obtained was 99.9% e.e.

Industrial Applicability

In accordance with the present invention constituted as above, an N-protected-S-phenylcysteine of high quality can be isolated expediently and efficiently in good yield.

What is claimed is:
1. A method for isolation of an N-protected-S-phenylcysteine represented by the following formula (1):

wherein $R^1$ represents an amino-protecting group; $R^2$ represents a hydrogen atom or, either independently of $R^1$ or taken together with $R^1$, represents an amino-protecting group, which comprises causing said N-protected-S-phenylcysteine to be salted out in the form of a base salt in the presence of water.

2. The method for isolation according to claim 1 wherein the salting out is carried out under a basic condition.

3. The method for isolation according to claim 1 wherein the salt used for the salting out is an inorganic salt.

4. The method for isolation according to claim 3 wherein the inorganic salt is an alkali metal salt.

5. The method for isolation according to claim 4 wherein the inorganic salt is sodium chloride or sodium sulfate.

6. The method for isolation according to claim 1, wherein the cation of the salt to be used for the salting out is the same species as the cation of the base salt of N-protected-S-phenylcysteine to be salted out.

7. The method for isolation according to claim 3, wherein the inorganic salt is used in a sufficient amount to effect salting out.

8. The method for isolation according to claim 7 wherein the inorganic salt is used in a concentration of not less than 5 weight % based on water.

9. The method for isolation according to claim 3, wherein the salting out of the base salt of N-protected-S-phenylcysteine in the presence of said inorganic salt is effected by
  i) increasing the amount of presence of said base salt of N-protected-S-phenylcysteine with the amount of presence of said inorganic salt being kept constant,
  ii) increasing the amount of presence of said inorganic salt, with the amount of presence of said base salt of N-protected-S-phenylcysteine being kept constant, or
  iii) increasing the amount of said base salt of N-protected-S-phenylcysteine, with the amount of presence of said inorganic salt being simultaneously increased.

10. The method for isolation according to claim 7, wherein the base salt of an N-protected-S-phenylcysteine is caused to form in an aqueous medium containing said inorganic salt in a sufficient amount to effect the salting out under a basic condition and, at the same time, the thus-formed N-protected-S-phenylcysteine salt is salted out.

11. The method for isolation according to claim 10 wherein a compound of the following formula (2):

(2)

wherein $R^1$ represents an amino-protecting group, $R^2$ represents a hydrogen atom or, either independently of $R^1$ or taken together with $R^1$, represents an amino-protecting group; X represents a leaving group, is treated with thiophenol in an aqueous medium containing said inorganic salt in a sufficient amount to effect salting out under a basic condition to give an N-protected-S-phenylcysteine and, at the same time, cause the base salt of N-protected-S-phenylcysteine formed to be salted out from the reaction mixture.

12. The method for isolation according to claim 1, wherein the salting out is carried out in the presence of a seed crystal.

13. The method for isolation according to claim 1, wherein an organic solvent is caused to be present at or after salting out for dissolution and removal of a fat-soluble contaminant.

14. A method of preparing a mixture of an organic solvent and a free N-protected-S-phenylcysteine which comprises causing an N-protected-S-phenylcysteine represented by the following formula (1):

(1)

wherein $R^1$ represents an amino-protecting group; $R^2$ represents a hydrogen atom or, either independently of $R^1$ or taken together with $R^1$, represents an amino-protecting group, to be salted out in the form of a base salt in the presence of water, and neutralizing, with an acid, the base salt of N-protected-S-phenylcysteine, to give the free N-protected-S-phenylcysteine and, then, mixing said free N-protected-S-phenylcysteine with an organic solvent.

15. The method according to claim 1, wherein the base salt of N-protected-S-phenylcysteine is a metal salt of the N-protected-S-phenylcysteine.

16. The method according to claim 15 wherein the metal salt of N-protected-S-phenylcysteine is an alkali metal salt of the N-protected-S-phenylcysteine.

17. The method according to claim 16 wherein the alkali metal salt of N-protected-S-phenylcysteine is a sodium salt of the N-protected-S-phenylcysteine.

18. The method according to claim 1, wherein the amino-protecting group is an urethane-type protective group.

19. The method according to claim 18 wherein the amino-protecting group is an aralkyloxycarbonyl group or a lower alkoxycarbonyl group.

20. The method according to claim 19 wherein the amino-protecting group is a benzyloxycarbonyl group, a tert-butoxycarbonyl group, a methoxycarbonyl group or an ethoxycarbonyl group.

21. The method according to claim 20 wherein the amino-protecting group is a benzyloxycarbonyl group.

* * * * *